United States Patent [19]
Davis

[11] Patent Number: 6,044,859
[45] Date of Patent: Apr. 4, 2000

[54] VALVE APPARATUS AND METHOD

[76] Inventor: Ralph L. Davis, R.R. 1 40512 Bloomfield Rd., Genoa City, Wis. 53128

[ * ] Notice: This patent issued on a continued prosecution application filed under 37 CFR 1.53(d), and is subject to the twenty year patent term provisions of 35 U.S.C. 154(a)(2).

[21] Appl. No.: 08/808,008

[22] Filed: Mar. 3, 1997

[51] Int. Cl.⁷ .............................. F16L 55/18; F16K 15/16
[52] U.S. Cl. ....................... 137/15; 137/846; 137/850; 604/247
[58] Field of Search .................. 137/846, 15, 850, 137/843, 844, 847; 604/247

[56] References Cited

U.S. PATENT DOCUMENTS

| | | | |
|---|---|---|---|
| 558,606 | 4/1896 | Hardman | 137/846 X |
| 615,751 | 12/1898 | Sands | 137/846 |
| 657,007 | 8/1900 | Richter | 137/846 X |
| 996,588 | 6/1911 | Kennedy | 137/846 |
| 1,282,075 | 10/1918 | Hand | 137/846 X |
| 2,328,382 | 8/1943 | Langdon | 137/846 |
| 3,118,468 | 1/1964 | Bochan | 137/525.1 |
| 3,556,122 | 1/1971 | Laerdal | 137/559 |
| 3,710,942 | 1/1973 | Rosenberg | 137/846 |
| 3,780,943 | 12/1973 | Lilja | 137/846 X |
| 3,855,995 | 12/1974 | Bentley | 137/846 X |
| 4,143,858 | 3/1979 | Abramson | 137/846 |
| 4,295,412 | 10/1981 | Hachiro | 137/551 |
| 4,473,094 | 9/1984 | Harris | 137/846 |
| 4,535,818 | 8/1985 | Duncan | 604/247 |
| 4,535,819 | 8/1985 | Atkinson | 137/846 |
| 4,612,960 | 9/1986 | Edwards | 137/846 |
| 4,725,266 | 2/1988 | Siposs | 604/247 |
| 4,749,003 | 6/1988 | Leason . | |
| 4,828,554 | 5/1989 | Griffin | 137/846 |
| 4,966,199 | 10/1990 | Ruschke . | |
| 5,010,925 | 4/1991 | Atkinson | 137/846 |
| 5,092,857 | 3/1992 | Fleischhacker | 137/846 |
| 5,176,173 | 1/1993 | McGarrah | 137/846 |
| 5,556,541 | 9/1996 | Ruschke . | |

FOREIGN PATENT DOCUMENTS 2830800  2/1979  Germany ................ 137/846

OTHER PUBLICATIONS

Check valve drawing dated Oct. 17, 1994, was supplied by a customer for redesign by Filtertec Inc. (one page).

Primary Examiner—Denise L. Ferensic
Assistant Examiner—Joanne Y. Kim
Attorney, Agent, or Firm—Brinks Hofer Gilson & Lione

[57] ABSTRACT

A valve includes an inlet and outlet housing, a flexible one-way valve, and a collar. The flexible valve is locked between the housings. The collar is attached to the inlet housing and extends into the flexible valve. As fluid flows through the valve, the collar supports the flexible valve and prevents collapse due to back flow pressure.

24 Claims, 2 Drawing Sheets

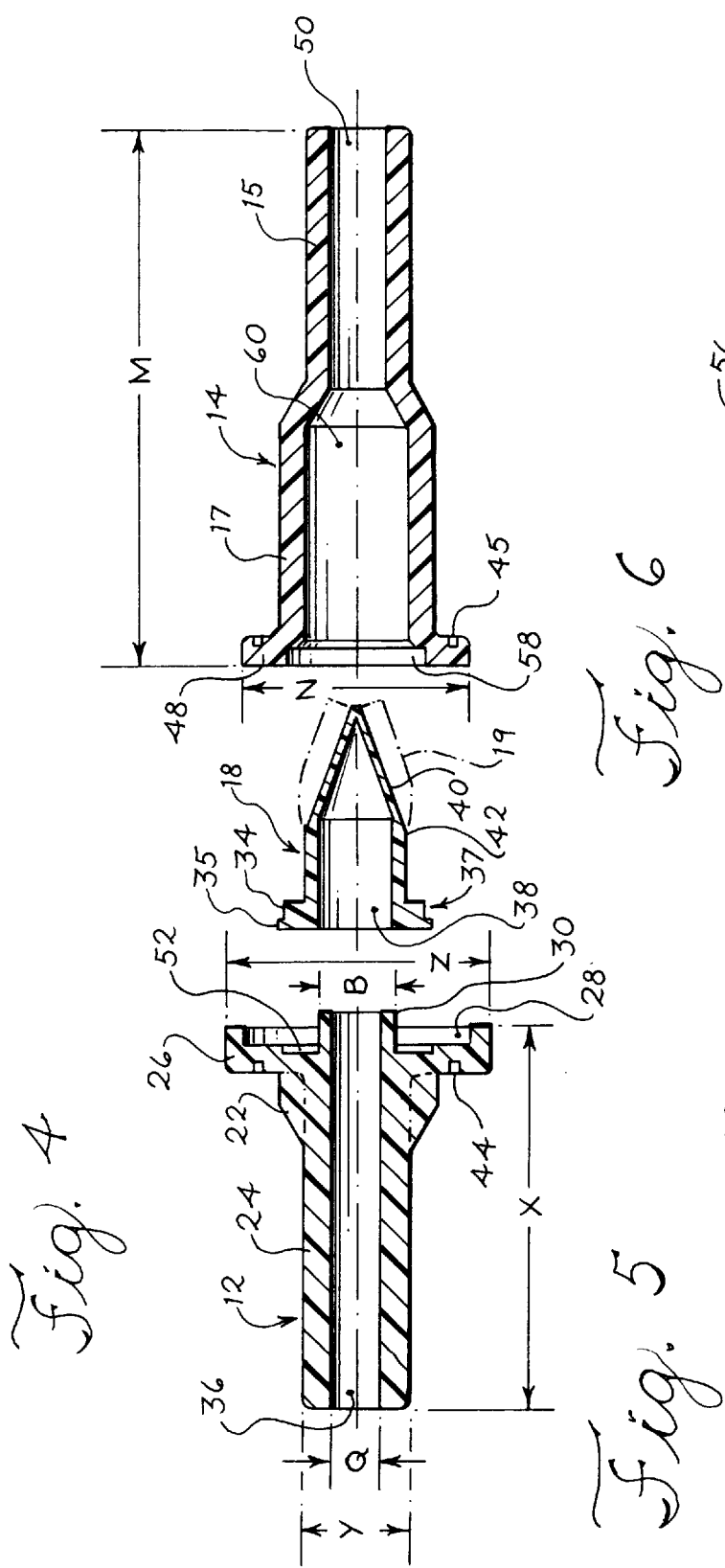
Fig. 4
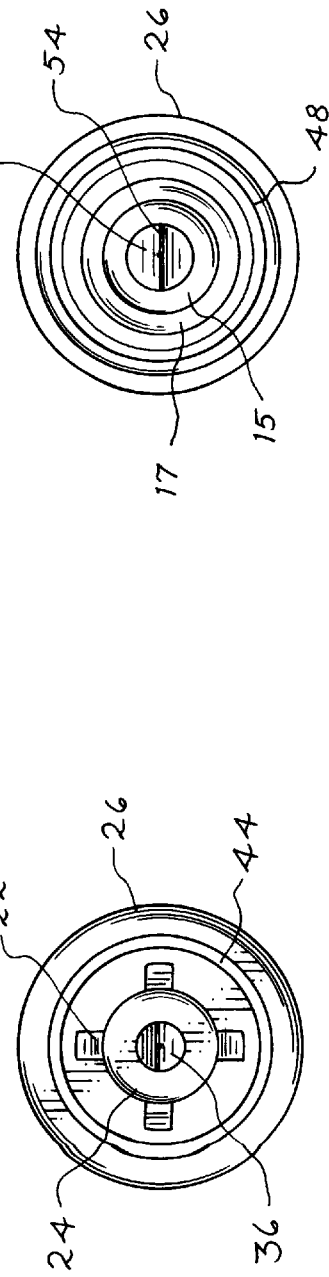
Fig. 6
Fig. 5

VALVE APPARATUS AND METHOD

FIELD OF THE INVENTION

The present invention relates to an improved check valve and process of manufacturing the same. More specifically, the invention relates to a check valve having a collar portion to support and prevent collapse of a flexible valve during usage.

BACKGROUND OF THE INVENTION

Check valves are well known in a variety of industries, including the medical industry. The purpose of such units is to allow blood or other fluids, including gases and liquids, to flow in only one direction. Under normal operating conditions the flow is prevented from reversing itself.

Under certain conditions, however, back pressure may build up to a level which may cause the check valve to collapse and fail.

In the medical field, for example, check valves are used in kidney dialysis machines which filter a patient's blood of waste products and excess water, and return the blood to the body. Normally, patients would check into the hospital three times a week to have their blood artificially cleaned. Check valves used in existing in-hospital dialysis machines are normally replaced after each use. Recent development in dialysis products now allow a patient to use a home dialysis system. This enables the patient to use the dialysis machine on a daily basis to help the patient's overall health and quality of life. In some dialysis machines, the components may be sanitized in place with steam. This requires the check valve components to withstand temperatures of 85° C. Many existing check valves would degrade under these high temperatures.

Check valves commonly include an inlet and outlet housing made of molded plastic and a flexible one-way or duckbill valve made of rubber or silicone. The flexible valve is aligned and secured between the housings. As fluid is passed through the check valve, a variety of conditions may cause back pressure to build up, causing the flow to attempt to reverse its direction. Existing check valves may fail due to collapse of the flexible duckbill valve, which may actually invert itself and allow the back flow of fluid to pass through the inlet. The flexible valve may also pull away from its original secured position between the housings. Accordingly, it would be desirable to have a check valve design that would withstand high back pressure spikes which commonly occur during usage.

SUMMARY OF THE INVENTION

One aspect of the invention provides a valve apparatus including an inlet housing member including an opening and a support portion, an outlet housing member including an opening and a support portion, and a collar extending from the support portion and including an opening in communication with the inlet housing member. The collar is configured to allow a flexible valve to be positioned over the collar portion. The apparatus may further include a flexible valve, preferably a duckbill valve, positioned over the collar portion. Preferably, the base portion of the duckbill valve is secured between the inlet housing and outlet housing, and the housings are sealed with an overmold band. The collar may extend into the duckbill valve at least about one sixth of the length of the duckbill valve. Preferably, the collar extends into the duckbill valve a distance sufficient to prevent collapse of the duckbill valve under pressure spikes of at least about four times normal back pressures, which for hemodialysis check valves may reach 30 psi. Preferably, the housing is made of a high density thermoplastic resin capable of withstanding temperatures in the range of 85° C., which is required for steam sanitation.

Another aspect of the invention provides for a method of operating the valve apparatus. A housing having an opening formed therein and a collar portion inside the housing and aligned with the opening is provided. A flexible valve fitted over the collar portion is also provided. A fluid is flowed through the opening and through the flexible valve. The valve is subjected to back pressure. The collar supports the flexible valve to prevent the back pressure from collapsing the valve.

Another aspect of the invention provides a valve apparatus including an inlet housing, an outlet housing, a flexible one-way valve, and a collar. The inlet housing includes a cylindrical shaft portion, a circular support portion, and an opening formed in the inlet housing. The outlet housing includes a cylindrical end portion, a valve housing portion, a base portion and an opening formed in the outlet housing. The base portion is in contact with the support portion and the openings are aligned. The flexible one-way valve includes a flange portion, a tapered portion, and an opening formed in the valve. The flange portion is locked between the base portion of the outlet housing and the support portion of the inlet housing. The collar is attached to the support portion of the inlet housing and extending into the valve opening. The apparatus may further include an overmold band formed over the support portion of the inlet housing and base portion of the outlet housing. The valve apparatus may also include a recessed area formed in the support portion for receiving the flange portion of the flexible valve. Preferably, the collar and inlet housing are formed as a monolithic member. The housings and collar may preferably be made of a high density polypropylene resin. The flange portion of the flexible valve may preferably be compressed between the base portion of the outlet housing and the support portion of the inlet housing in an axial direction. The flange portion of the flexible valve may also preferably be compressed between the collar and the base portion of the outlet housing in a radial direction. The valve apparatus may further include an arrow inscribed on an outer surface of the outlet housing to indicate the direction of fluid flow during normal operation. Preferably, the housings are made of a clear material which allows a user to view fluid flow. A plurality of ribs extending axially from the support portion and radially from the shaft portion of the inlet housing may stabilize the support portion and reduce bending during usage of the check valve. Preferably, the collar extends into the flexible valve opening at least about one sixth of the length of the flexible valve. The desired length of the collar will vary based on flow conditions, back pressure conditions, material costs, and other factors determined by the check valve size, configuration and use.

Additional features and advantages are described in, and will be apparent from, the detailed description of the presently preferred embodiments and from the drawings.

BRIEF DESCRIPTION OF THE DRAWINGS

FIG. 4 is an exploded sectional view of the embodiment of FIG. 1, shown without the overmold band;

FIG. 5 is an end view of the inlet housing of FIG. 4; and
FIG. 6 is an end view of the outlet housing of FIG. 4.

DETAILED DESCRIPTION OF THE DRAWINGS AND PRESENTLY PREFERRED EMBODIMENTS OF THE INVENTION

Figure 1:
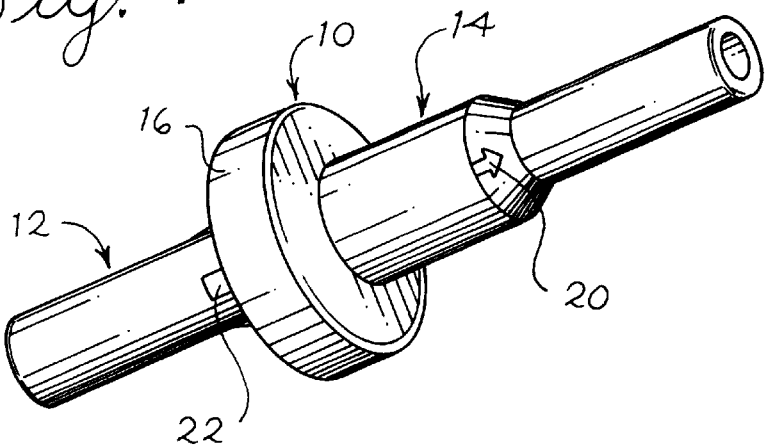
FIG. 1 is a perspective view of an embodiment of the check valve of the present invention.
Figure 2:
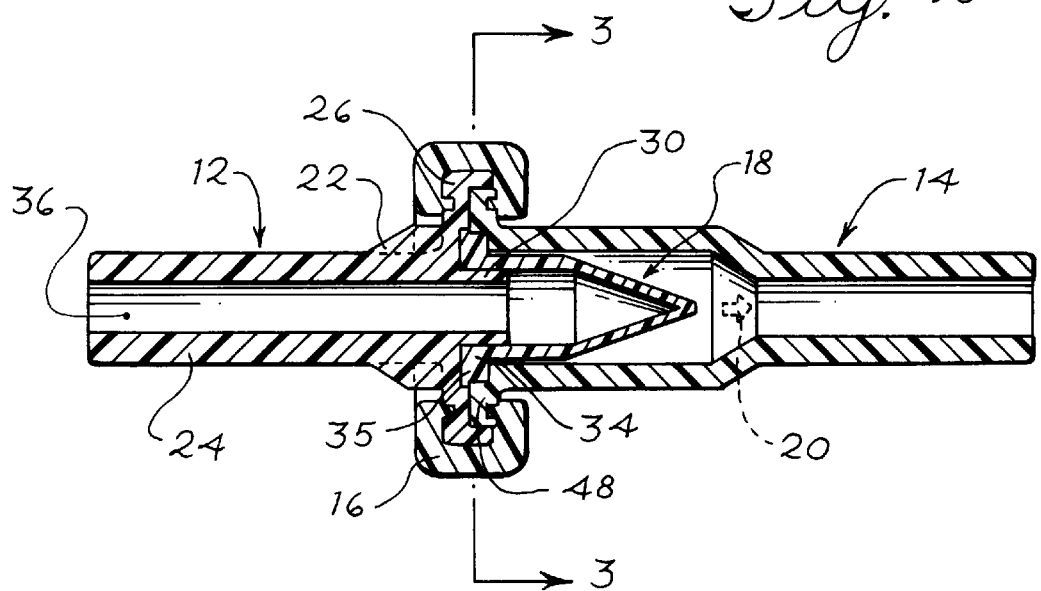
FIG. 2 is a sectional view of the embodiment of FIG. 1.
Figure 3:
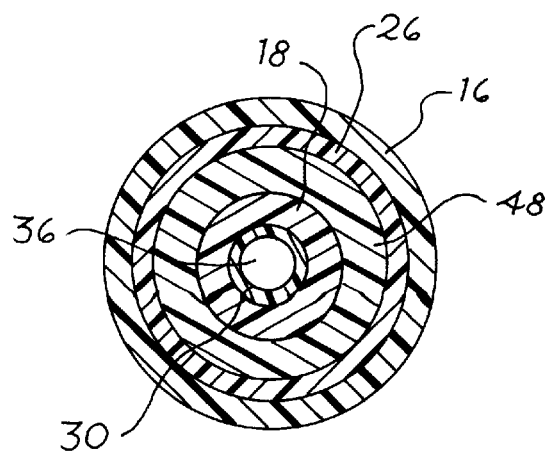
FIG. 3 is a sectional view taken along lines 3—3 of FIG. 2.

Referring to FIGS. 1 and 2, a preferred check valve 10 of the present invention includes an inlet housing 12, an outlet housing 14, a duckbill valve 18 and an overmold band 16. As shown in FIGS. 2–4, the inlet and outlet housings 12, 14 are aligned with each other and the duckbill valve 18. The inlet and outlet housings 12, 14 are made of a rigid material, preferably a clear material which will allow the user to observe fluid flowing through the housing members. Preferably, the housings are made of a thermoplastic which will withstand repeated exposure to temperatures of 85° C. and allow for in-place steam sanitation without significant deterioration. One example of such a thermoplastic is a high density polypropylene resin. The inlet housing 12 includes a cylindrical shaft portion 24 "configured to connect to medical tubing, circular support portion 26, and collar portion 30. The outlet housing 14 includes an end portion 15 "configured to connect to medical tubing, a valve housing portion 17 and a base portion 48.

In one embodiment, for example, the inlet housing 12 has a length X of 1.145 inches, measured from the inlet to the edge of the support portion 26, with the shaft portion 24 having an outer diameter Y of 0.315 inch, and the support portion 26 having an outer diameter Z of 0.789 inch. In this embodiment, the inlet orifice 36 has a diameter Q of 0.175 inch. The support portion includes a recessed region 28 with a diameter R to receive the base portion 48 of the outlet housing 14. A second recessed area 52 in the support portion 26 is designed to receive the rim 35 of the duckbill valve. The collar 30 has a length A, for the embodiment shown of ¼ inch measured from the recessed area 52. The collar 30 has an outer diameter B, of 0.255 inch and is received in the valve opening 38. The length of the collar 30 may vary depending on the intended use of the check valve. The ¼ inch collar, described above, supports the duckbill valve 18 and prevents collapse under back pressures, which may spike, for example, to 30 psi during the hemodialysis process. The collar 30 is preferably formed as a portion of the inlet housing 12, but may alternatively be formed as a separate member.

For this embodiment, the outlet housing 14 has a length M of 1.620 inches, with the end portion 15 having an outer diameter of 0.315 inch, the valve housing portion 17 having an outer diameter of 0.465 inch, and the base portion 48 having an outer diameter N of 0.684 inch. The outlet housing base portion 48 is received in the recessed area 52 of the support portion 26. The duckbill valve 18 is a standard one-way valve having a tapered portion 40, a cylindrical portion 42 and a flange portion 37. The flange portion 37 includes base portion 34 and a rim portion 35. As shown in FIG. 6, the duckbill valve has a slit 54 and a flat tapered area 56 which forms the duckbill. The remainder of the tapered portion 40 has a tapered and curved surface, and the cylindrical body portion 42 is cylindrical. Preferably, the duckbill valve 18 is made of a soft rubber or silicone and, for the embodiment shown, has a length of about ⅝ inch. For example, Vernay Laboratories of Yellow Springs, Ohio supplies duckbill valves suitable for use in this embodiment of the check valve.

As shown in FIGS. 2 and 3, as assembled, the cylindrical body portion 42 of the duckbill valve fits within the inner chamber 60 of the valve housing portion 17. The base and rim portions 34, 35 of the duckbill valve 18 are received within the recessed regions 52 and 58 and between the base portion 48 and support portion 26. The collar portion 30 extends into the valve opening 38. Preferably, the collar 30 extends at least above one sixth of the length of the flexible valve 18. Alternatively, the collar may extend further into the cylindrical portion 42 of the flexible valve 18. With some flexible valves, the collar may extend only far enough so that the outlet housing 14 may radially compress the flexible valve 18 against the collar 30. Once assembled, overmold material, which is a compatible thermoplastic material, is injected around the support portion 26 and base portion 48 and flows into the support and base grooves 44, 45. The overmold band 16 locks and hermetically seals the housings and secures the flexible valve base and rim portions 34, 35 in a compressed state.

As shown in FIG. 5, rib members 22 extend radially from the shaft 24 and axially from the support portion 26. The ribs 22 add structural support to the inlet housing 12 and reduce bending under pressure, which might otherwise act to release the rim and base portions 34, 35 of the duckbill valve, causing the valve to collapse.

In operation, fluid is passed through the inlet orifice 36, through the flexible valve (shown in its open position by dashed lines 19 in FIG. 4) and through the outlet orifice 50, as indicated by arrow 20. The duckbill valve 18 remains in place even with extreme pressure spikes, which, for example, may reach 30 psi under same condition during hemodialysis. As secured by the overmold band 16, the base portion 48 of the outlet housing 14 compresses the base 34 and rim 35 of the flexible valve 18 axially against the support portion 26 of the inlet housing 12 and radially against the collar 30. The ribs 22 further stabilize the support portion 26 and reduce bending during high back pressure conditions, and help prevent the flexible valve 18 from pulling away from its secured position between the housings.

It should be appreciated that the apparatus and methods of the present invention are capable of being incorporated in the form of a variety of embodiments, only one of which has been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

I claim:

1. A check valve apparatus for allowing the continuous one-way flow of fluid through the apparatus for use with medical equipment or procedures, said apparatus comprising:

a) an inlet housing member including a cylindrical shaft having an opening formed therein and a support portion, the shaft comprising a medical tubing connector, the opening for allowing fluid to flow into and through the inlet housing member;

b) an outlet housing member having a unitary construction and including a cylindrical shaft having an opening formed therein and a base portion seated against the support portion, the shaft comprising a medical tubing connector, the opening for allowing fluid to flow through and out from the outlet housing member; and c) a collar extending perpendicular from the support portion and including an opening formed therein in communication with the inlet housing member opening, the collar being configured to receive a flexible valve including a flange portion and a cylinder portion extending perpendicular from a surface of the flange portion, and to radially support an interior surface of the cylinder portion, and to allow the flange portion to be contacted by and secured between the support portion and the base portion.

2. The valve apparatus of claim 1 further comprising a flexible valve positioned over the collar portion.

3. The valve apparatus of claim 2 wherein the flexible valve comprises a duckbill valve.

4. The valve apparatus of claim 3 wherein the flange portion of the duckbill valve is secured between the inlet housing and outlet housing and the housings are sealed with an overmold.

5. The valve apparatus of claim 3 wherein the collar extends at least about one sixth of the length of the duckbill valve positioned over the collar.

6. The valve apparatus of claim 1 wherein the collar extends a distance sufficient to prevent collapse of a duckbill valve under pressure spikes of at least about 30 psi.

7. The apparatus of claim 1 wherein the inlet housing member and outlet housing member are sealed together with an overmold.

8. The apparatus of claim 1 wherein the housings are made of high density thermoplastic capable of withstanding temperatures in the range of 85° C.

9. A method of operating a check valve apparatus in a medical procedure comprising:

a) providing an inlet housing member including a cylindrical shaft comprising a medical tubing connector and having an opening formed therein and a support portion, an outlet housing member including a cylindrical shaft comprising a medical tubing connector and having an opening formed therein and a base portion seated against the support portion and a collar portion inside the housing and aligned with the opening, and a flexible valve including a flange portion and a cylinder portion extending perpendicular from a surface of the flange portion fitted between the collar portion and the support portion, the collar portion extending perpendicular from the support portion to support an interior surface of the cylinder portion, the flange portion contacted by and secured between the support portion and base portion;

b) flowing a fluid continuously through the apparatus by flowing the fluid through the opening in the inlet housing member, through the flexible valve, and through the opening in the outlet housing member;

c) subjecting the valve to back pressure; and d) supporting the flexible valve with the collar to prevent the back pressure from collapsing the valve.

10. A check valve apparatus for allowing the continuous one-way flow of fluid through the apparatus for use with medical equipment or procedures, said apparatus comprising:

a) an inlet housing including a cylinder shaft portion, a medical tubing connector, a circular support portion, and an opening formed in the inlet housing, the opening for allowing, fluid to flow into and through the inlet housing;

b) an outlet housing having a unitary construction and including a cylinder end portion, a medical tubing connector, a valve housing portion, a base portion, and an opening formed in the outlet housing, the opening for allowing fluid to flow through and out from the outlet housing, the base portion being in contact with the support portion of the inlet housing; and the openings being aligned with one another;

c) a flexible one-way valve including a flange portion, a cylinder portion extending perpendicular from a surface of the flange portion, a tapered portion extending from the cylinder portion, and an opening formed in the valve, the flange portion locked between the base portion of the outlet housing and the support portion of the inlet housing; and d) a collar attached to and extending perpendicular from the support portion of the inlet housing, and the collar extending beyond the flange portion into the valve opening and contacting an interior surface of the cylinder portion.

11. The valve apparatus of claim 10 further comprising an overmold band formed over the support portion of the inlet housing and the base portion of the outlet housing.

12. The valve apparatus of claim 10 further comprising a recessed area formed in the support portion for receiving a base portion of the flexible valve.

13. The valve apparatus of claim 10 wherein the collar and inlet housing are formed as a monolithic member.

14. The valve apparatus of claim 13 wherein the housings and collar are made of a high density polypropylene resin.

15. The valve apparatus of claim 10 wherein the flange portion of the flexible valve is compressed between the base portion of the outlet housing and the support portion of the inlet housing in an axial direction.

16. The valve apparatus of claim 15 wherein the flange portion of the flexible valve is compressed between the collar and the base portion of the outlet housing in a radial direction.

17. The valve apparatus of claim 10 further comprising an arrow inscribed on an outer surface of the outlet housing to indicate the direction of fluid flow under normal operation.

18. The valve apparatus of claim 10 wherein the housings are made of a clear material which allows a user to view fluid flowing through the apparatus.

19. The apparatus of claim 10 further comprising a plurality of ribs extending axially from the support portion and radially from the shaft portion of the inlet housing.

20. The apparatus of claim 10 wherein the collar extends into the flexible valve opening at least about one sixth of the length of the flexible valve.

21. A hemodialysis system comprising a check valve apparatus connected to a dialysis machine by medical tubing, said check valve apparatus comprising:

a) an inlet housing member having a cylindrical shaft and a support portion, said cylindrical shaft comprising a medical tubing connector, said inlet housing further comprising an opening formed therein for allowing a fluid received from the medical tubing to flow through the inlet housing member;

b) an outlet housing member having a unitary construction and including a cylindrical shaft and a base portion, said cylindrical shaft comprising a medical tubing connector, said base portion being seated against the support portion of said inlet housing member, said outlet housing member further comprising an opening formed therein for allowing a fluid to flow through the outlet housing member and into the medical tubing;

c) a flexible valve member comprising a flange portion and a cylinder portion extending perpendicularly from a surface of the flange portion, said flange being contacted by and secured between the support portion of said inlet housing member and the base portion of said outlet housing member; and d) a collar extending perpendicular from the support portion of said inlet housing member and including an opening formed therein in communication with the inlet housing member opening, the collar being configured to receive the flexible valve member and support an interior surface of said cylinder portion so as to prevent said flexible valve member from collapsing when subjected to back pressure.

22. The hemodialysis system of claim 21 wherein the inlet housing member and the outlet housing member of said check valve apparatus are sealed together with an overmold.

23. The hemodialysis system of claim 21 wherein the collar of said check valve apparatus extends into the cylinder portion of the flexible valve member a distance of at least about one sixth of the length of said flexible valve member.

24. The hemodialysis system of claim 21 wherein the inlet and outlet housings of said check valve apparatus are made from high density thermoplastic capable of withstanding temperatures of about 85° C.

\* \* \* \* \*

UNITED STATES PATENT AND TRADEMARK OFFICE
CERTIFICATE OF CORRECTION

PATENT NO. : 6,044,859
DATED : April 4, 2000
INVENTOR(S) : Ralph L. Davis

It is certified that error appears in the above-identified patent and that said Letters Patent is hereby corrected as shown below:

On the Title Page

In column 1, after item [76], insert a new item as follows:

--Assignee: Filtertek Inc., Hebron, Ill.--.

In claim 10, line 8, delete "," (comma) immediately after "allowing".

In claim 12, line 2, delete "receiving a" and substitute --receiving the-- in its place.

Signed and Sealed this

First Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,044,859
DATED : April 4, 2000
INVENTOR(S) : Ralph L. Davis

It is certified that error appears in the above-identified patent and that said Letters Patent is hereby corrected as shown below:

Title page,
Insert Item:
-- [73]   Assignee: Filterteck Inc., Hebron, Ill. --.

Column 5,
Line 64, delete "," (comma) immediately after "allowing".

Column 6,
Line 23, delete "receiving a " and substitute -- receiving the -- in its place.

Signed and Sealed this

Fifth Day of October, 2004

JON W. DUDAS
*Director of the United States Patent and Trademark Office*